United States Patent
Chen et al.

(10) Patent No.: US 11,988,620 B2
(45) Date of Patent: May 21, 2024

(54) METHOD TO DETERMINE AN UNCORRUPTED NUCLEAR MAGNETIC RESONANCE RESPONSE FROM A SAMPLE

(71) Applicant: ARAMCO SERVICES COMPANY, Houston, TX (US)

(72) Inventors: Jin-Hong Chen, Katy, TX (US); Stacey M. Althaus, Houston, TX (US); Mohammed Boudjatit, El Kennar (DZ); Gary Eppler, Baytown, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 96 days.

(21) Appl. No.: 17/814,170

(22) Filed: Jul. 21, 2022

(65) Prior Publication Data
US 2024/0027378 A1  Jan. 25, 2024

(51) Int. Cl.
*G01N 24/08* (2006.01)
*E21B 44/00* (2006.01)
*E21B 47/06* (2012.01)
*E21B 49/02* (2006.01)
*G01N 15/08* (2006.01)
(Continued)

(52) U.S. Cl.
CPC ........... *G01N 24/081* (2013.01); *E21B 44/00* (2013.01); *E21B 47/06* (2013.01); *E21B 49/02* (2013.01); *G01N 15/082* (2013.01); *G01N 33/24* (2013.01); *G01V 20/00* (2024.01); *E21B 7/04* (2013.01); *E21B 2200/20* (2020.05)

(58) Field of Classification Search
CPC .... G01N 24/081; G01N 15/082; G01N 33/24; E21B 44/00; E21B 47/06; E21B 49/02; E21B 7/04; E21B 2200/20; G01V 99/005
See application file for complete search history.

(56) References Cited

U.S. PATENT DOCUMENTS 9,482,631 B2   11/2016 Yang et al.
9,828,820 B2   11/2017 Gupta et al.
(Continued)

OTHER PUBLICATIONS

Z. Gu et al.; "NMR Response of Methane in Gas Shale", URTeC: 2438441; Unconventional Resources Technology Conference; Aug. 1, 2016; pp. 1-5 (5 pages).

*Primary Examiner* — G. M. A Hyder
(74) *Attorney, Agent, or Firm* — Osha Bergman Watanabe & Burton LLP (57) ABSTRACT

A method and system for determining an uncorrupted NMR response from a sample at a predetermined measurement pressure is provided. The method includes obtaining a sample and a filler fluid with a negligible NMR response, determining a volume of filler fluid based on a dimension of the sample and an interior volume of a pressure cell, injecting the volume of filler fluid at a first temperature into the pressure cell and then changing the temperature of the volume of the filler fluid to a second temperature. The method also includes inserting the sample into the volume of filler fluid within the pressure cell, displacing an upper surface of filler fluid to a predetermined level within the interior volume of the pressure cell. The method still further includes establishing the predetermined measurement pressure within the pressure cell and determining the uncorrupted NMR response from the sample at the predetermined measurement pressure.

18 Claims, 7 Drawing Sheets

(51) Int. Cl.
G01N 33/24 (2006.01)
G01V 20/00 (2024.01)
*E21B 7/04* (2006.01)

(56) References Cited

U.S. PATENT DOCUMENTS

2017/0089158 A1* 3/2017 Gupta .................... G01N 33/24
2021/0140902 A1   5/2021 Badri et al.

* cited by examiner

METHOD TO DETERMINE AN UNCORRUPTED NUCLEAR MAGNETIC RESONANCE RESPONSE FROM A SAMPLE

BACKGROUND

In the petroleum industry, hydrocarbons are located in reservoirs far beneath the surface of the Earth. Wells are drilled into these reservoirs to access and produce the hydrocarbons. As a wellbore is created beneath the surface of the Earth, rock core samples or rock plug samples are often extracted and brought to the surface for examination. In conventional coring, a cylindrical section of rock is cut and removed from the path of the wellbore by a coring bit. A second coring technique, termed "sidewall coring", may also be used to extract a rock core sample. In sidewall coring, mechanical tools may use hollow rotary drills to cut through the sidewall rock formation producing "rotary sidewall cores". The rock core sample may be examined to determine a reservoir characteristic, including by nuclear magnetic resonance (NMR). A reservoir characteristic may incorporate any of the characteristics pertinent to the reservoirs ability to store and produce hydrocarbons and may be input to reservoir modelers. Reservoir modelers are used to produce a reservoir model of a subterranean region of interest. The reservoir model may be used to create a reservoir simulation of the behavior of rocks and fluids under various hydrocarbon recovery scenarios to find a drilling target.

NMR analyses measure interaction of nuclear spins of atoms within the rock core sample when the sample is placed in a powerful magnetic field. NMR analyses can be used to analyze a rock core sample to determine several reservoir characteristics pertinent to reservoir characterization, including porosity, permeability, and the types and quantities of fluids present. These characteristics may be used as inputs to a reservoir model and the reservoir model may, in turn, be used by a reservoir simulator to determine an advantageous production technique for a drilling operation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method for determining an uncorrupted NMR response from a sample at a predetermined measurement pressure is provided. The method includes obtaining a sample and a filler fluid with a negligible NMR response, determining a volume of filler fluid based on a dimension of the sample and an interior volume of a pressure cell, injecting the volume of filler fluid at a first temperature into the pressure cell and then changing the temperature of the volume of the filler fluid to a second temperature. The method also includes inserting the sample into the volume of filler fluid within the pressure cell, displacing an upper surface of filler fluid to a predetermined level within the interior volume of the pressure cell. The method still further includes establishing the predetermined measurement pressure within the pressure cell and determining the uncorrupted NMR response from the sample at the predetermined measurement pressure.

In general, in one aspect, embodiments relate to an NMR system that includes a pressure cell comprising a sealable open end, a closed end and an interior volume. The NMR system also includes a volume of filler fluid with a negligible NMR response configured to be injected inside the interior volume of the pressure cell at a first temperature and a sample configured to be insertable into the pressure cell through the sealable open end and into the filler fluid at a second temperature. The sample displaces an upper surface of filler fluid to a predetermined level within the interior volume of the pressure cell when inserted. The NMR system includes an NMR pressure and injection system configured to establish a predetermined measurement pressure within the pressure cell. The NMR system further includes and a NMR control and data acquisition system configured to determine an uncorrupted NMR response from the sample at the predetermined measurement pressure and determine a reservoir characteristic of the sample based, at least in part, on the uncorrupted NMR response. The reservoir characteristic comprises a porosity, a composition, a water and a hydrocarbon content, a permeability, or a behavior of an injected fluid in accordance with one or more embodiments. The system also includes a reservoir modeler configured to produce a reservoir model based on the reservoir characteristic, a reservoir simulator configured to produce a reservoir simulation to determine a drilling target based on the reservoir model, a wellbore path planning system configured to plan a wellbore path to intersect the drilling target of a subterranean region of interest and a wellbore drilling system configured to drill a wellbore guided by the wellbore path.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-7 any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

The embodiments disclosed herein describe a method to determine an uncorrupted NMR response from a sample at a predetermined measurement pressure using an NMR system. Traditional NMR analyses include measuring NMR responses from a sample inserted into a pressure cell. In the traditional design, an annular space or interior volume exists between the sample and the inner wall of the pressure cell within a sensitive region of an NMR coil. During the NMR analysis, fluids are often injected into the sample. The NMR signal or response from the injected fluids in the interior volume, within this sensitive region can produce their own signal that may overlap with the signal from the sample and make determining a reservoir characteristic, such as porosity, permeability, pore size, or pore fluid, difficult.

Embodiments disclosed herein describe a method that may reduce or eliminate this unwanted NMR contribution from the interior volume of the pressure cell, by filling the pressure cell with a hydrogen-free filler fluid that has a negligible NMR response. By replacing an otherwise empty annular space or interior volume with this hydrogen-free filler fluid having a negligible NMR response, the potential for injected fluids to occupy this interior volume within the sensitive region of an NMR coil, during NMR analyses may be reduced or eliminated. With no injected fluids occupying the interior volume, there will be no unwanted NMR response detected. The NMR signal recorded using the addition of the filler fluid is therefore an uncorrupted NMR signal.

Using a rock core as the sample, the uncorrupted NMR response may be processed and interpreted to determine one or more reservoir characteristics, that may be input into a reservoir modeler to produce a reservoir model. The reservoir model may include information about the total hydrocarbon in place and how effectively the hydrocarbons can potentially flow through the formation. The reservoir model may be used to create a reservoir simulation that predicts the behavior of rocks and fluid under various hydrocarbon recovery scenarios. In accordance with one or more embodiments, a drilling target may be determined based on the reservoir simulation and a wellbore path may be planned using a wellbore path planning system based, at least in part, on the drilling target.

Embodiments disclosed herein allow for an estimation of reservoir reserve which is a key parameter and is always required to evaluate a reservoir. More specifically, the experiment setup described herein may be used to estimate gas-in-place and also estimate the flow rate when gas is injected from top of the rock core. Both types of parameters are critical in evaluating and producing a petroleum reservoir.

Figure 1:
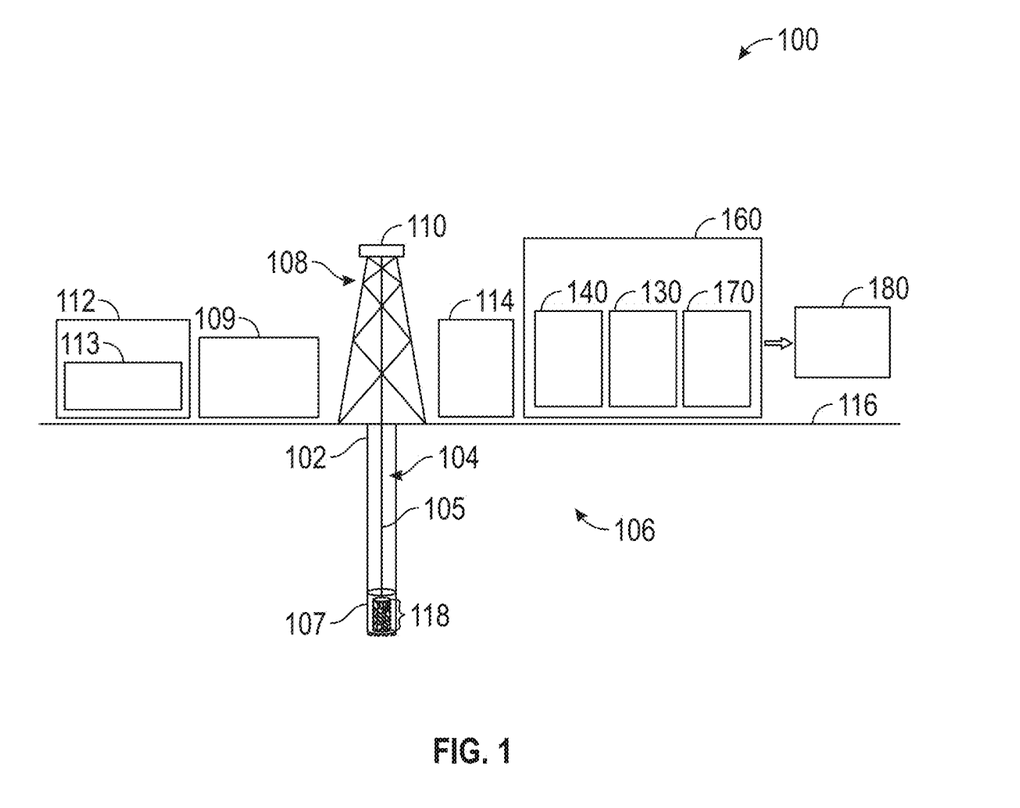
FIG. 1 depicts a well site in accordance with one or more embodiments.

FIG. 1 depicts a well site (100) in accordance with one or more embodiments, that may include a well (102) having a wellbore (104) extending into a formation (106). The wellbore (104) may include a bored hole that extends from the surface (116) into a target zone of the formation (106), such as a reservoir (not shown). The well site (100) may include a drilling system (108), a logging system (112), a control system (114), a reservoir modeler (160) and a reservoir simulator (180).

The drilling system (108) may include a well (102), a mud circulation system (109) to inject drilling fluids into the wellbore (104) and a coring bit (107) attached by a drillstring (105) to a coring rig (110). The formation (106) may be cored to produce rock core samples (118) or rock plug sample for analysis. Coring operations may include physically extracting a rock core sample (118) from a region of interest within the wellbore (104) by a coring bit (107) and bring it to Earth's surface (116) to be examined. The rock core samples (118), usually cylindrical, may be analyzed in a laboratory to determine various reservoir characteristics (130) from the location from which the sample was obtained.

The rock core sample (118) may be examined to determine a variety of reservoir characteristics (130) relevant to reservoir characterization including porosity, permeability, or the presence of hydrocarbons. Porosity may indicate how much void space or pore space exists in a particular rock within the formation (106), where oil, gas or water may be trapped. Permeability may indicate the ability of liquids and gases to flow through the rock within the area of interest. The rock core samples (118) may be examined at the well site (100) or sent to a laboratory to perform different analyses, including NMR spectroscopy, to determine a reservoir characteristic (130).

The control system (114) may include hardware and/or software for managing drilling operations and/or maintenance operations. For example, the control system (114) may include one or more programmable logic controllers (PLCs) that include hardware and/or software with functionality to control one or more processes performed by the drilling system (108).

The logging system (112) may include one or more logging tools (113), such as a nuclear magnetic resonance (NMR) logging tool or a resistivity logging tool, for use in generating well logs (140) of the formation (106). For example, a logging tool may be lowered into the wellbore (104) to acquire measurements as the tool traverses a depth interval. The plot of the logging measurements versus depth may be referred to as a "log" or "well log". Well logs (140) may provide depth measurements of the well (102) that describe such reservoir characteristics as formation porosity, formation permeability, resistivity, water saturation, and the like. The resulting logging measurements may be stored or processed or both, for example, by the control system (114), to generate corresponding well logs (140) for the well (102).

NMR logging measures the induced magnetic moment of hydrogen nuclei (specifically, protons) contained within the fluid-filled pore space of porous media (for example, reservoir rocks). Thus, NMR logs may measure the magnetic response of fluids present in the pore spaces of the reservoir rocks. In so doing, NMR logs may measure both porosity and permeability as well as the types of fluids present in the pore spaces, which is important for reservoir.

In some embodiments, a reservoir modeler (160) comprises functionality for simulating the flow of fluids, including hydrocarbon fluids such as oil and gas, through a formation composed of porous, permeable reservoir rocks. The reservoir modeler (160) may combine information determined from well logs (140), reservoir characteristics (130) determined from rock core samples (118) and any other geological models (170) available to build models of the reservoir. The reservoir models may include information total hydrocarbon in place, where the hydrocarbons are located, and how effectively the hydrocarbons can potentially flow.

In some embodiments, a reservoir simulator (180) may be configured to accept a reservoir model and produce a reservoir simulation to predict the behavior of rocks and fluid under various hydrocarbon recovery scenarios, allowing reservoir engineers to understand which recovery options offer the most advantageous hydrocarbon recovery plan for a given reservoir. A drilling target, or a chosen location to penetrate the hydrocarbon reservoir, may be determined through reservoir simulation by estimating the flow rate, or the fluid flow within the reservoir given various drilling target scenarios.

The reservoir simulator (180) may include hardware and/or software with functionality for performing one or more reservoir simulations regarding the hydrocarbon-bearing formation (106). Drilling decisions may be made on the well site (100), including determining an updated drilling target, based at least part, on the reservoir simulation. While the reservoir modeler (160) and reservoir simulator (180) are shown at a well site (100), in some embodiments, the reservoir modeler (160) and the reservoir simulator (180) may be remote from a well site. In some embodiments, the reservoir modeler (160) is implemented as part of a software platform for the control system (114). The software platform may obtain data acquired by the drilling system (108) and logging system (112) as inputs, which may include multiple data types from multiple sources. The software platform may aggregate the data from these systems (108, 112) in real time for rapid analysis. In some embodiments, the control system (114), the logging system (112), the reservoir modeler (160) and/or the reservoir simulator (180) may include a computer system that is similar to the computer system (702) described below with regard to FIG. 7 and the accompanying description.

NMR or NMR spectroscopy is a valuable analysis technique used on a variety of different sample objects in a variety of industries. NMR is the study of molecules by recording the interaction of radiofrequency (Rf) electromagnetic radiations with the nuclei of molecules placed in a strong magnetic field. When molecules, at an initial equilibrium state, are placed in a strong magnetic field, as in standard NMR spectroscopy techniques, the nuclei of some atoms (such as the proton forming a hydrogen $^1H$ nucleus) will begin to behave like small magnets. If a broad spectrum of radio frequency waves is applied to the sample, or an Rf pulse, the nuclei will begin to resonate at their own specific frequencies or resonant frequencies. This is called magnetic resonance and is achieved when the nuclei are irradiated with radiofrequency. The Rf pulse is then switched off, and the molecules return to their initial equilibrium state. A 'relaxation time' may recorded based on these molecules returning to their initial equilibrium states.

NMR analysis techniques may determine multiple signals for analyzing a sample, such as a rock core sample. First, an NMR analysis may determine spin-lattice relaxation values or a T1 signal amplitude that is measured from the buildup of magnetization along a static applied magnetic field. T1 signal values may be mainly related to pore size and viscosity. Likewise, a T1 signal may be measured using inversion recovery or saturation recovery, where the T1 signal may be characterized as the loss of resonance intensity following a pulse excitation.

Furthermore, an NMR analysis may also determine transverse relaxation values or a T2 signal amplitude that describes the decay of an excited magnetization perpendicular to an applied magnetic field. The T2 signal may refer to the decaying time for protons to complete dephasing. Likewise, NMR measurements may be illustrated as a T2 signal amplitude versus time and determine a distribution of porosity components (i.e., a T2 distribution) as a function of their T2 times. Thus, a T2 signal amplitude may be proportional to hydrogen content within a core sample and thus may determine porosity independent of the rock matrix. Both relaxation times may provide information for determining pore-size information and pore-fluid properties, especially viscosity.

Figure 5A:
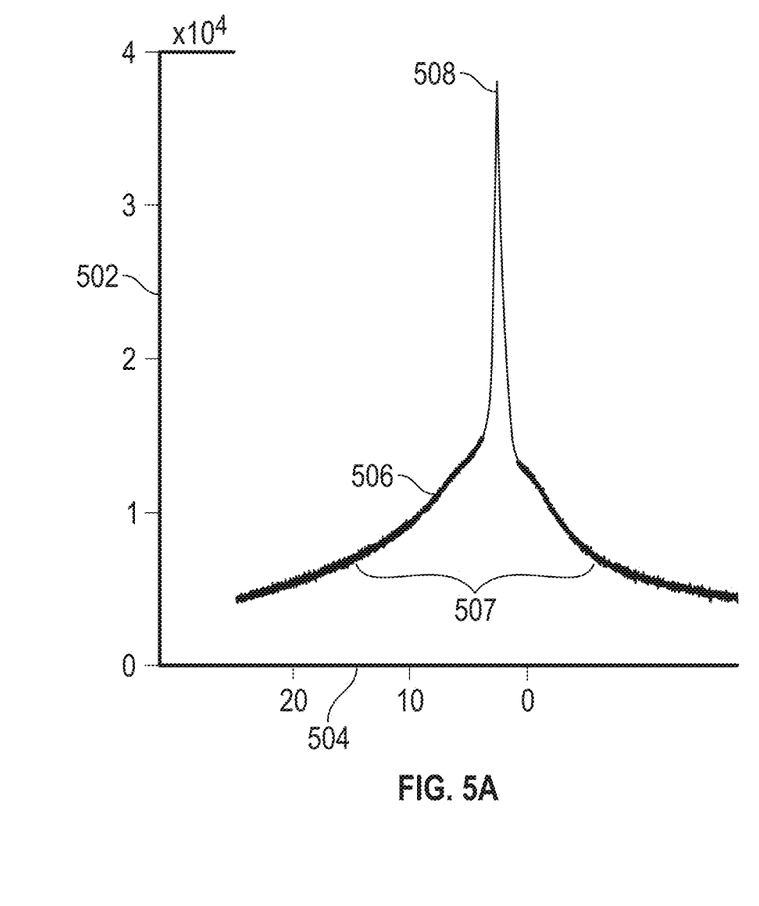
FIGS. 5A and 5B show an NMR spectrum in accordance with one or more embodiments.
Figure 5B:
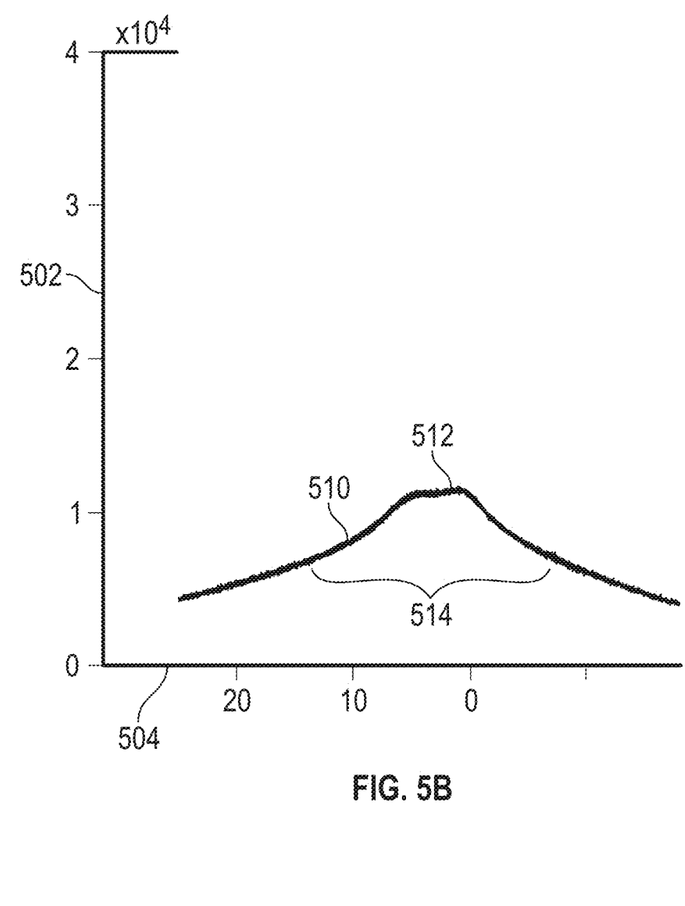

As a consequence of this relaxation, energy is emitted as radiofrequency, producing a characteristic signal called free induction decay (FID). The FID is the observable NMR signal that is generated. This FID is subsequently transformed into a plot of intensities versus frequencies known as an NMR spectrum. An NMR spectrum is illustrated in FIG. 5A and FIG. 5B. The location of the NMR signal on the spectrum, in relation to a benchmark, is called the chemical shift. The chemical shift is defined by the frequency of the resonance expressed with a reference to this benchmark or standard. For NMR experiments measuring $^1H$, Tetramethylsilane [TMS;$(CH_3)_4Si$] is generally used for this benchmark to determine chemical shift of compounds: $\delta_{TMS}=0$ ppm. That is, chemical shift is represented as parts per million (ppm) relative to Tetramethylsilane. A sample's chemical shift may also be indicative of several factors relating to a reservoir characteristic, including estimating a porosity and viscosity.

Before a sample is examined in pressurized NMR analyses, it may be inserted inside a pressure cell. A pressure cell may house the sample and withstand an elevated measurement pressure during NMR analyses. The embodiments disclosed herein describe the addition of a filler fluid to a pressure cell, prior to the insertion of the sample, to determine an uncorrupted NMR response of the sample at a predetermined measurement pressure.

Figure 2A:
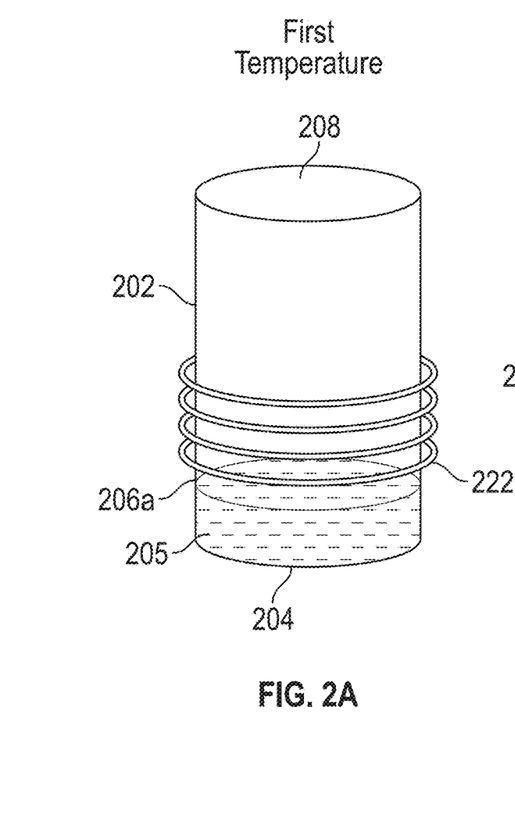
FIGS. 2A-2C depict a sample inserted into a pressure cell in accordance with one or more embodiments.
Figure 2B:
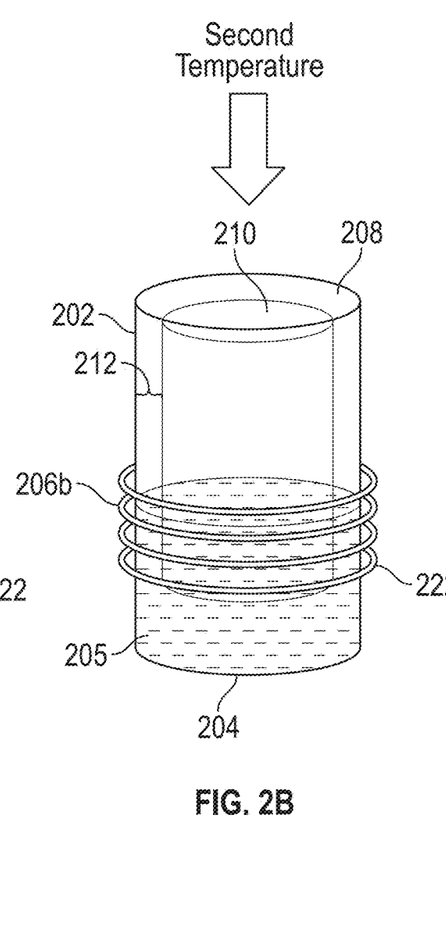
Figure 2C:
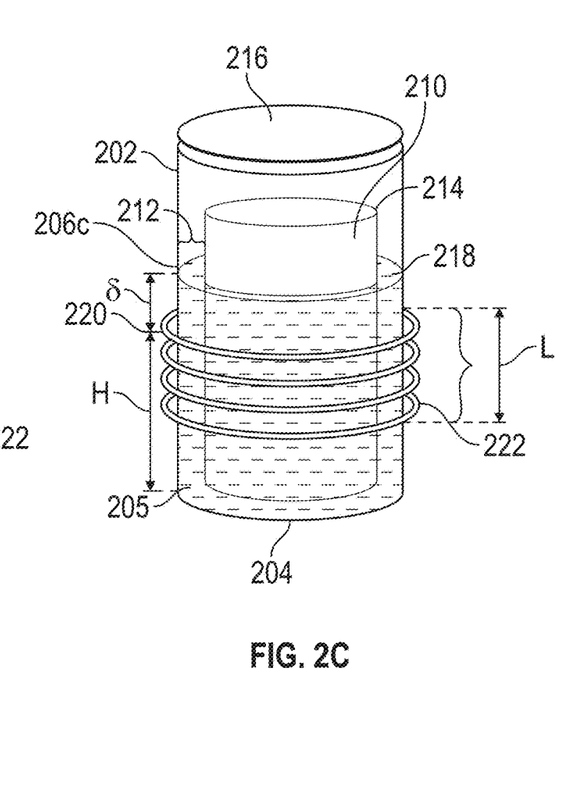

FIGS. 2A-2C illustrate the injection of filler fluid (205) into a pressure cell (202), the insertion of a sample (210) into a volume of filler fluid (205) and the sealing of the pressure cell (202). A pressure cell (202) is used to house the sample (210) and a volume filler fluid (205). The pressure cell (202) is able to sustain a predetermined measurement pressure during NMR analyses. The filler fluid (205) comprises a hydrogen-free filler fluid, including Halocarbon 1000N. The filler fluid (205) may be any fluid that has a negligible NMR response or no NMR response during NMR analyses. A traditional NMR system does not include the use of this filler fluid (205) as seen in FIGS. 2A-2C.

In FIG. 2A a volume of filler fluid (205) at a first temperature may be injected into a pressure cell (202) through the open end (208) of the pressure cell (202). The NMR coil (222) is shown wrapped around the pressure cell (202). At the first temperature the filler fluid (205) may have a sufficiently low viscosity to allow its injection and to settle to the closed end (204) and to fill the pressure cell (202) to a first surface level (206a). Prior to the insertion of the sample (210) into the pressure cell (202) and the displacement of a portion of the volume of filler fluid (205) the volume of filler fluid (205) may be brought to a second temperature. At the second temperature, that may typically be a lower temperature than the first temperature, the viscosity of the filler fluid (205) may be higher than its viscosity at the first temperature. Consequently, the filler fluid (205) may resist flow under a pressure gradient. In particular, the filler fluid (205) at the second temperature may resist flow into the pores of a porous sample.

FIG. 2B depicts the insertion of a sample (210) through the open end (208) of the pressure cell (202) into the volume of filler fluid (205) with the pressure cell (202). The inserted sample (210) may displace the filler fluid (205) into the annulus (212) formed between the interior wall of the pressure cell (202) and the exterior surface of the sample (210). As the filler fluid (205) is displaced the upper surface (206b) of the filler fluid (205) rises within the annulus. The increased viscosity of the filler fluid (205) at the second temperature prevents, or strongly inhibits, the flow of filler fluid (205) into the pores of the sample (210).

FIG. 2C shows the sample (210) after complete insertion into the pressure cell (202). The previously open end (208) of the pressure cell (202) is closed with a seal (216). The seal may secure the sample (210) and filler fluid contained within the pressure cell (202) and allow the pressure within the pressure cell (202) to be raised to an elevated pressure. The surface of the filler fluid (206c) may be displaced by the sample (210) to a predetermined level (218) selected to be below the upper surface of the sample (214) when fully inserted into the pressure cell (202) and above the top NMR coil surface (220) of the NMR coils (222) when the pressure cell is inserted into the NMR system. The volume of filler fluid (205) may be selected in conjunction with the interior diameter of the pressure cell (202) and the exterior diameter of the sample so that the surface (206c) of the filler fluid (205) reaches the predetermined level (218) when the sample is fully inserted into the pressure cell (202).

The predetermined level (218) is defined by having a final height relationship H+δ, shown in FIG. 2C. First, the final height of the filler fluid (205) at the predetermined level (218) must be higher than a top NMR coil surface (220). The top NMR coil surface (220) marks the end of the sensitive region of the NMR coil. Secondly, the height of the filler fluid (205), or H+δ, must also be smaller than the length of the sample, $l_{samp}$, so that injected fluids may be injected into the sample from the top of the pressure cell to study the samples injections with the injected fluids. FIG. 2C also shows the sensitive region of the NMR coil (L). No empty interior volume (212) is shown within the NMR coil (L) sensitive region, therefore no NMR response is expected from injected fluids in the interior volume (212) of the pressure cell during NMR analyses. Furthermore, FIG. 2C shows the pressure cell (202) ready for insertion into the center of the superconducting magnets of the NMR system to begin measuring an uncorrupted NMR response.

Figure 3:
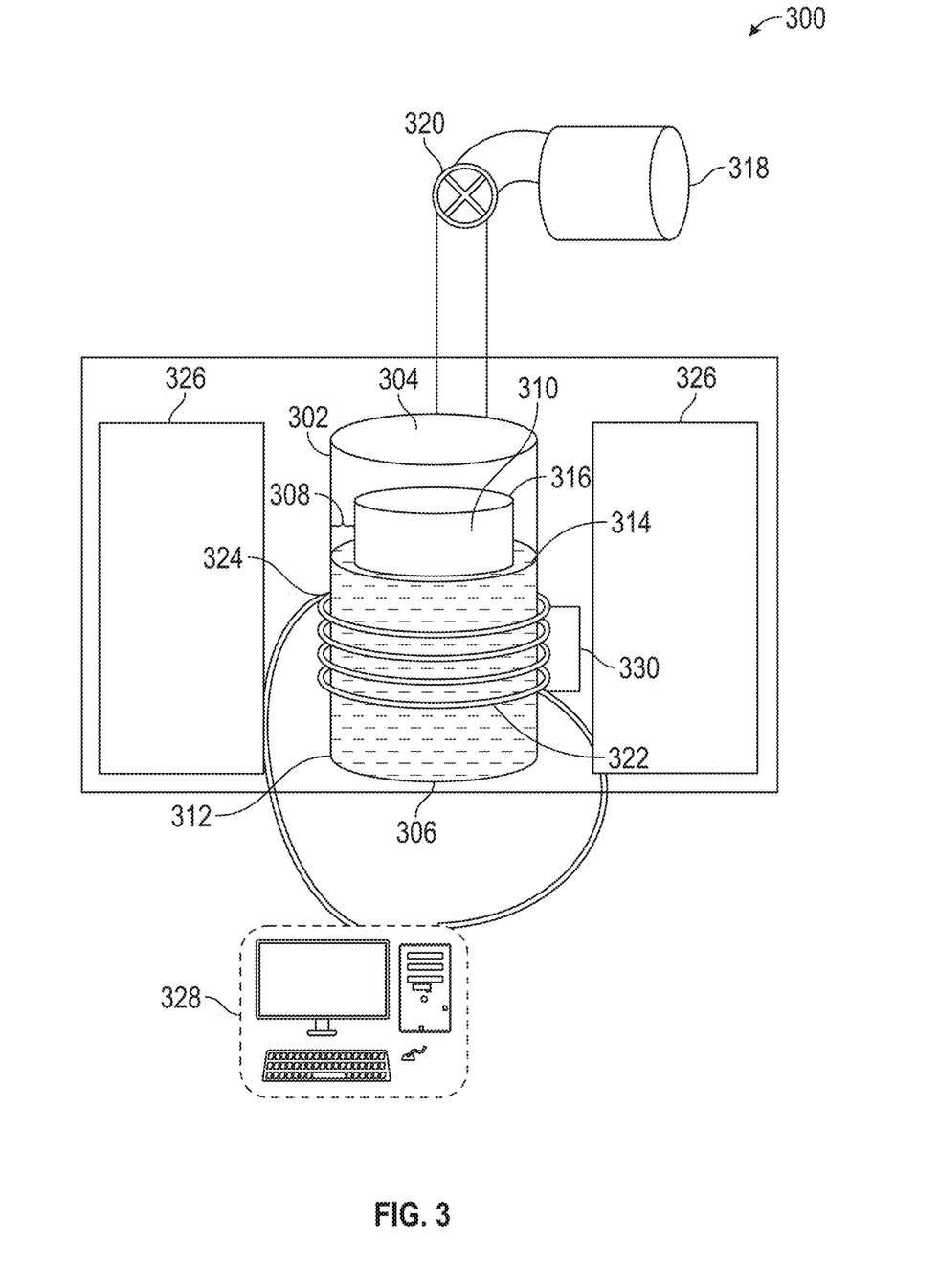
FIG. 3 depicts an NMR system in accordance with one or more embodiments.

FIG. 3 depicts an NMR system (300) in accordance with one or more embodiments. An NMR system (300) includes a pressure cell (302) comprising a sealable open end (304) a closed end (306) and an interior volume (308) or an annular volume. FIG. 3 shows the sample (310) fully inserted into the pressure cell (302) containing the filler fluid (312) at a second temperature, illustrated previously in FIG. 2C. The sample (310) may be a rock core sample, in accordance with one or more embodiments. The upper surface of the filler fluid is displaced by the sample (310) to a predetermined level (314) selected to be below the upper surface of the sample (316) when fully inserted into the pressure cell (302) and above the top NMR coil surface (324) of the NMR coils (322) when the pressure cell (302) is inserted into the NMR system (300). The volume of filler fluid (312) may be determined based on a dimension of the sample and the interior volume (308) of the pressure cell (302) in accordance with one or more embodiments. The function of the filler fluid (312) and method to determine the required volume will be discussed in greater detail in the context of FIG. 4.

NMR is routinely used to study the fluid distribution and transport in the pore networks in rock core samples. Many of these studies are required to be at reservoir conditions at pressures that reach more than 10,000 PSI. An injected fluid (318), or a hydrocarbon fluid may be injected into the pressure cell (302) by an NMR pressure and injection system (320), to establish the desired predetermined measurement pressure. The injected fluid (318) may be methane gas, representing one of the hydrocarbon gases that are typically used to establish this desired measurement pressure. The injected fluid (318) used in NMR analyses is dependent on the interest of study and may be chosen to determine the behaviour of that specific injected fluid (318) within the pores of the sample. By chosing a hydrocarbon gas such as methane to be injected at a predetermined measurement pressure, NMR analyses may represent reservoir conditions that may indicate the hydrocarbon fluid distribution and transport in the pore networks in a rock core sample.

The NMR system (300) includes a superconducting magnet or magnets (326). The superconducting magnets may be two separate magnets as shown in FIG. 3, or one large magnet with a center opening, allowing for the insertion of the pressure cell (302). During traditional NMR analyses, the sample (310) located inside the pressure cell (302) is placed in the center of the superconducting magnet (326). The superconducting magnet (326) is responsible for the generation of a strong magnetic field that aligns the nuclear spins of the atoms present in the sample (310).

The NMR system (300) also includes an NMR coil (322) having a top NMR coil surface (324). The NMR coil (322) is magnetic and generates a magnetic field whenever current flows through it. The NMR coil (322) is used to irradiate the radiofrequency pulses and to detect and collect the NMR signal emitted by the sample. NMR coils (322) also enable control of the magnetic field homogeneity and the application of pulse gradients that are used in some NMR analyses. The top NMR coil surface (324) indicates the height at which the NMR coil is no longer able to be sensitive to NMR measurements. The NMR coil (322) does not react to any NMR signal above this top NMR coil surface (324). The length of the sensitive region of the NMR coil (330) is illustrated in FIG. 3.

The NMR control and data acquisition system (328) is responsible for data acquisition and subsequent mathematical transformation into an interpretable NMR spectrum. The NMR control and data acquisition system (328) may record the observable NMR signal that is generated by the NMR system (300), known as the FID. This FID may then be transformed, using the NMR control and data acquisition system (328) into a plot of intensities versus frequencies known as an NMR spectrum. This NMR spectrum, shown in FIG. 5, may be interpreted to determine several reservoir characteristics, for a rock plug sample (310). The NMR control and data acquisition system (328) may include a computer system that is similar to the computer system (702) described below with regard to FIG. 7 and the accompanying description. The NMR control and data acquisition system (328) may also be used to determine the volume of filler fluid based on a dimension of the sample and an interior volume of a pressure cell in accordance with one or more embodiments. An NMR system (300) may include additional features or omit any mentioned features in accordance with one or more embodiments, without departing from the novel aspect of the method.

To demonstrate a problem with traditional NMR analyses, a traditional NMR analysis is presented. A sample (310) is loaded in a pressure cell (302) and placed in an NMR coil (322). In this design, an annular space or interior volume (308) exists between the sample (310) and the inner wall of the pressure cell (302). This interior volume (308) is shown in FIG. 3 being occupied by a volume of filler fluid (312), however during traditional NMR analyses, the interior volume (308) is empty. When an injected fluid (318) is injected into the sample (310) inside the pressure cell (302) it also fills this interior volume (308). The injected fluid (318) in the interior volume produces a measureable NMR response. This NMR response from the interior volume fluid can overlap with the signal from the sample (310) and makes the study of the pore fluid very difficult, if not impossible. In this traditional NMR analysis, methane gas was injected into the pressure cell (302) containing a rock sore sample (310) to a pressure of 75 PSI prior to obtaining the NMR spectrum. The NMR signals from the rock core sample (310) and the injected fluid (318) are overlapped at the same chemical shift in an NMR spectrum. The NMR spectrum is corrupted by the injected fluids (318) presence in this interior volume. For rock core samples (310) that are characterized by having a very low porosity, such as shales, the contribution from the injected fluids (318) from the interior volume (308) will have negative impact on the measured NMR response.

This overlap in NMR signals corrupt the NMR response obtained and may give inaccurate information as to the rock core samples porosity, permeability, or other reservoir characteristics. To demonstrate the problem, the ratio of contribution of signals from the interior volume (308) and from the sample (310) is given by:

$$r = \frac{[\pi(d_{cell}^{ID}/2)^2 - \pi(d_{plug}/2)^2] \times L}{\pi(d_{plug}/2)^2 \times L \times \phi}$$ Equation (1)

where r is the ratio of the contribution of signals from the interior volume (308) over the contribution of signals from the sample (310); $d_{cell}^{ID}$ and $d_{samp}$ are the inner diameter of the pressure cell and the diameter of the sample, respectively; L is the length of the sensitive region of the NMR coil (330); $\phi$ is the porosity of the plug. Eq. (1) can be simplified to:

$$r = [(d_{cell}^{ID}/d_{plug})^2 - 1]/\phi$$ Equation (2)

From the relationships determined in Equation (2), as the porosity decreases in rock core samples (310), the ratio of the contribution of signals from the interior volume (308) to the contribution of signals from the rock core sample (310) increases.

In this traditional NMR analyses, using a 5 millimeter (mm) NMR probe coil, $d_{cell}^{ID}$=3.6 mm and $d_{samp}$=3.4 mm, the ratio r is determined to be 1.2 for the rock with 10 porosity units (p.u.) and 2.4 for the rock with 5 p.u. Porosity units (p.u.) are a unit of measurement that is equal to the percentage of pore space in a unit volume of rock. Therefore, the signal contribution from the injected fluid (318) in the interior volume (308) to the overall detected NMR signal is comparable or much larger than the NMR signal detected from the sample (310) itself. This makes the accurate measurement of signals from the sample (310) extremely difficult and sometime impossible as the NMR response is corrupted. This is especially true for rock core samples (310) that are characterized by having a very low porosity such as shales. In order to determine an uncorrupted NMR response from a sample (310) at a predetermined measurement pressure, the signal contribution from the injected fluid (318) in the interior volume (308) may be greatly reduced or eliminated. The disclosure described herein, describes a method to determine an uncorrupted NMR response from a sample (310) at a predetermined measurement pressure.

Figure 4:
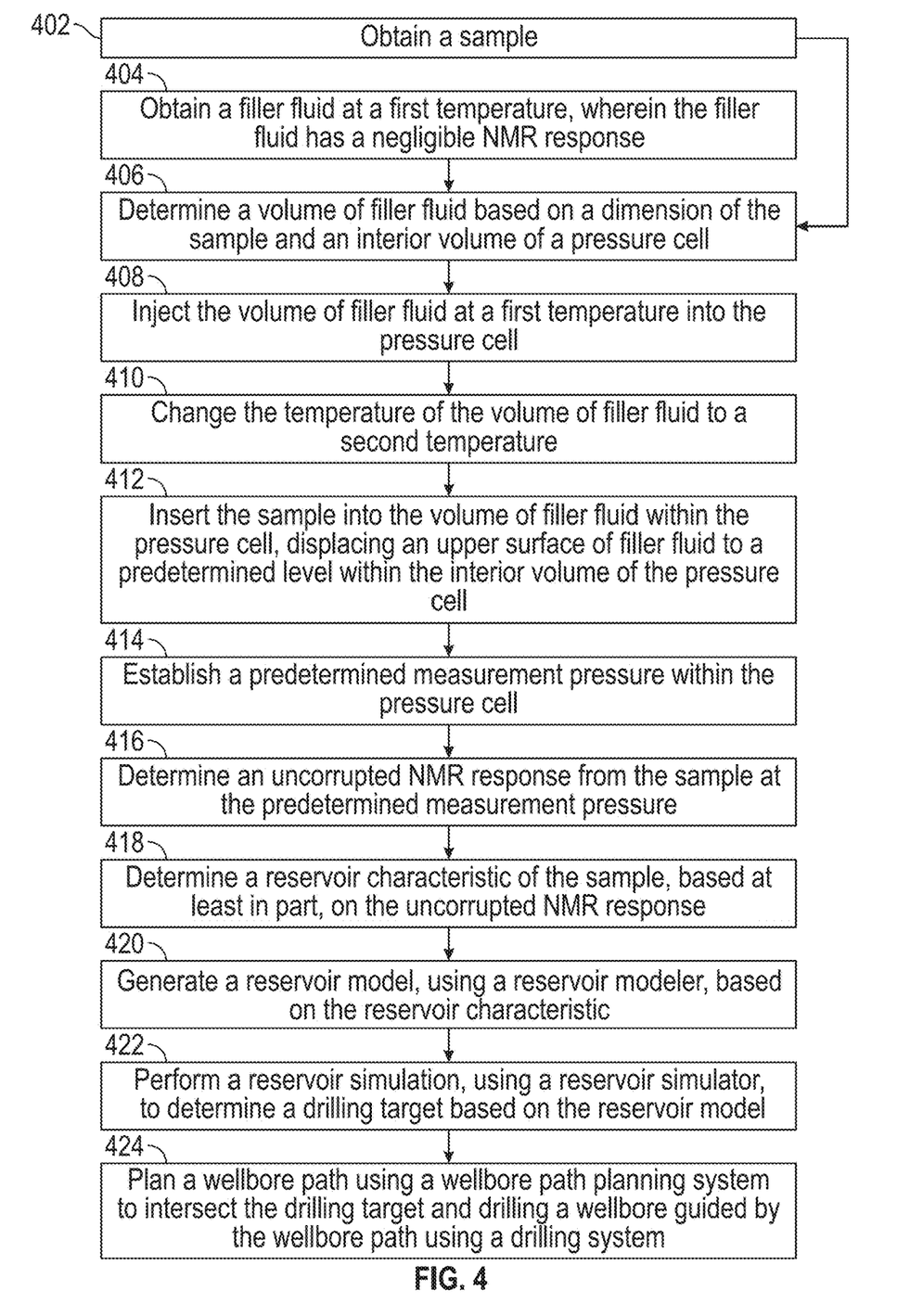
FIG. 4 shows a flowchart in accordance with one or more embodiments.

FIG. 4 shows a flowchart describing the method for determining an uncorrupted NMR response from a sample at a predetermined measurement pressure. In Step 402, a sample may be obtained in accordance with one or more embodiments. The sample may be a rock core sample, extracted from a subterranean region of interest by coring, as described by FIG. 1. The sample may also be any solid or semi-solid porous material in which NMR analyses are performed on without departing from the scope of this method. In addition to the oil and gas industry, NMR measurements may be utilized for a variety of materials expanding many industries. For example, NMR experiments may be used in food science, to check for quality or authenticity of food samples or in health science to study the porosity of bones. In addition, any references in the following equations that represent the volume of the sample as a cylinder, should understand that the volume of the sample may be determined based on the dimensions of that sample. Furthermore, the sample is not restricted to being of a cylinder shape.

In Step 404 a filler fluid is obtained at a first temperature, wherein the filler fluid has a negligible NMR response in accordance with one or more embodiments. The filler fluid comprises a hydrogen-free filler fluid. The hydrogen-free filler fluid may comprise Halocarbon 1000N in accordance with one or more embodiments. Different filler fluids may be used during NMR analyses; however the filler fluid must satisfy several requirements.

The first requirement is that the filler fluid cannot contain a detectable NMR signal. NMR experiments used in the study of rock core samples detect $^1$H (hydrogen with a single atom), therefore the filler fluid must comprise of 'a hydrogen-free filler fluid' or a fluid that contains no hydrogen. The filler fluid must also be sufficiently viscous so that invasion into the rock core is negligible. NMR analyses on rock core samples often measure the NMR response of injected materials in the pore space of rocks. Therefore, the filler fluid must be sufficiently viscous, whenever in contact with the rock core sample, as to not intrude into the pore space. The filler fluid may also possess a range of viscosities dependent on temperature, in accordance with one or more embodiments. In NMR experiments involving an injected fluid, using a filler fluid with a viscosity larger than 500 centipoise (cp) is sufficient whenever the filler fluid is in contact with the sample.

One such filler fluid that satisfies all of the necessary requirements is Halocarbon 1000N. Halocarbon 1000N is an inert oil and more specifically a high molecular weight polymer of chlorotrifluoroethylene (PCTFE). Halocarbon contains no hydrogen and generates a negligible NMR response during NMR analyses. Halocarbon 1000N also displays a high range of viscosities dependent on temperature. For example, Halocarbon 1000N has a viscosity of 1000 cp at room temperature (approximately 22° Celsius (C)) but becomes much less viscous at higher temperatures and much more viscous at lower temperatures. Halocarbon having a high range of viscosities dependent on temperature allows for easy handling of this fluid at different steps in the disclosed method. The filler fluid may be obtained at any temperature, however subsequent steps of the method require the filler fluid to be at a certain temperature, to ensure a desired viscosity.

Although Halocarbon 1000N is used as an example in this disclosure, as it satisfies all of the requirements of the filler fluid, other types of Halocarbons may be used under different experimental conditions. Other types of fluids other than Halocarbon may also be used, with the understanding that all the requirements for the filler fluid are satisfied.

In Step 406 a volume of filler fluid is determined based on a dimension of the sample and an interior volume of a pressure cell in accordance with one or more embodiments. The volume of filler fluid is determined by a final height relationship of the filler fluid in the interior volume of the pressure cell, H+δ, wherein H is the distance from the closed end of the pressure cell to the top NMR coil surface, and δ is the distance from the top of H to the predetermined level within the interior volume of the pressure cell. The predetermined level is located above a top NMR coil surface and below a top surface of the sample, when the sample is fully inserted into the filler fluid. The volume of filler fluid is determined based on two criteria. First, the height of the filler fluid, H+δ, in the interior volume must be higher than a top NMR coil surface. Secondly, the height of the filler fluid, H+δ, must also be smaller than the length of the sample, $l_{samp}$, so that fluids may be injected into the sample to study the samples interaction with the injected fluids. Based on the criteria given, the filler fluid volume is determined by:

$$v = [\pi(d_{cell}^{ID}/2)^2 - \pi(d_{samp}/2)^2] \times (H+\delta) \quad \text{Equation (3)}$$

where H+δ<$l_{samp}$. Therefore, determining a volume of filler fluid, is determining the volume of filler fluid required to reach a predetermined level within the interior volume of the pressure cell, when displaced by a sample. The volume of filler fluid at the predetermined level, H+δ, is illustrated in FIG. 2C. Step 406 may be performed before Step 404 in accordance with one or more embodiments.

In Step 408 the volume of filler fluid is injected into the pressure cell, wherein the filler fluid is at a first temperature, in accordance with one or more embodiments. Step 408 is illustrated in FIG. 2A, which shows the volume of filler fluid injected into the pressure cell at the first temperature. The viscosity of the filler fluid at the first temperature is sufficiently low to enable an injection of the filler fluid into the pressure cell. The injection of the filler fluid at the first temperature is so that all of the fluid may be injected easily and settle at the closed end of the pressure cell. The filler fluid may be injected into the pressure cell by a syringe, a pipette, or by any other means without deviating from the novel aspect of this method. For example, the syringe may be a long needle syringe. Similarly, the pipette may be a narrow tip pipette. The viscosity of the filler fluid at the first temperature may be between 5 cp and 500 cp in order to ensure a successful injection. The filler fluid is injected through an open end of the pressure cell and the injection process may conclude when the entirety of the volume of filler fluid is disposed at the closed end of the pressure cell. The physical injection of the filler fluid may be performed by any method, including a syringe, without deviating from the scope of this method. Any method may be used to increase the temperature of the filler fluid prior to the injection if necessary, including using an oven in accordance with one or more embodiments.

In Step 410 the temperature of the volume of the filler fluid is changed to a second temperature in accordance with one or more embodiments. The viscosity of the filler fluid at the second temperature is sufficiently high to prevent invasion of the filler fluid into the pores within the sample. Any method to change the temperature of the filler fluid inside the pressure cell may be used, including placing the pressure cell containing the filler fluid in a cooler to speed the process. In NMR analyses using a rock core sample, injected fluids are measured within the pore space of the rock core sample, revealing certain reservoir characteristics. The filler fluid must not invade within the pore space of the sample to accurately determine these reservoir characteristics, therefore the filler fluid is changed to a second temperature.

In Step 412 the sample is inserted into the volume of filler fluid within the pressure cell, displacing an upper surface of filler fluid to a predetermined level within the interior volume of the pressure cell, in accordance with one or more embodiments. Step 412 is illustrated in FIG. 2B, which shows the active insertion of the sample into the volume of filler fluid within the pressure cell, while the filler fluid is at the second temperature. The sample is inserted through an open end of the pressure cell into the filler fluid disposed at a closed end of the pressure cell. The predetermined level within the interior volume of the pressure cell, expressed as H+δ, was determined by Step 406, in determining the volume of filler fluid. The height of the filler fluid, H+δ, in the interior volume must be higher than a top NMR coil surface. Secondly, the height of the filler fluid, H+δ, must also be smaller than the length of the sample, $l_{samp}$. This predetermined level is determined so that the filler fluid, having a negligible NMR response, occupies the portion of the interior volume of the pressure cell, that is readable by the sensitive portion of the NMR coil. The length of the sample being longer than the predetermined level ensures successful injection of an experimental liquid or gas, into the pores of the sample. With the sample and filler fluid at a second temperature in the pressure cell, the pressure cell may now be sealed at the open end and inserted into the center of the superconducting magnets.

In Step 414 a predetermined measurement pressure is established within the pressure cell, in accordance with one or more embodiments. The predetermined measurement pressure may comprise a hydrocarbon reservoir pressure. NMR analyses performed on rock core samples are often carried out at a predetermined measurement pressure representing a hydrocarbon reservoir pressure. In order to perform the most accurate NMR analyses to obtain reliable reservoir characteristics, the experiments must replicate the samples reservoir pressure. One of the ways this is accomplished, is by injecting an injected fluid into the sample, wherein the injected fluid is not dissolvable in the filler fluid at the predetermined measurement pressure. The injected fluid may be injected into the pressure cell to establish the predetermined measurement pressure using the NMR pressure and injection system, described by FIG. 3. In one or more embodiments, the injection pressure is controlled by the injection pump which is set at the desired gas pressure. The injected fluid may be a hydrocarbon fluid in accordance with one or more embodiments.

In Step 416 an uncorrupted NMR response from the sample at the predetermined measurement pressure is determined in accordance with one or more embodiments. The superconducting magnet is responsible for the generation of a strong magnetic field that aligns the nuclear spins of the atoms present in the sample. The NMR coil is used to detect and collect the NMR signal emitted by the sample. The NMR coils are able to detect any NMR signal that is included within the coil sensitive region. The addition of the filler fluid having a negligible NMR response, to the interior volume of the pressure cell prevents any NMR signal from an injected fluid from being detected by the NMR coils. The NMR system sends the signals to be recorded by the NMR control and data acquisition system. The NMR control and data acquisition system is responsible for data acquisition and subsequent mathematical transformation into an interpretable NMR spectrum or a plot of intensities versus frequencies. The NMR spectrum, shown in FIG. 5, may be interpreted to determine several reservoir characteristics, for a rock plug sample.

In Step 418 a reservoir characteristic of the sample is determined, based at least in part, on the uncorrupted NMR response in accordance with one or more embodiments. The reservoir characteristic may include a porosity, a composition, a water and a hydrocarbon content, a permeability, or a behavior of injected fluid. For example, in NMR analyses that involve an injection of a hydrocarbon fluid, such as methane gas, into a rock core sample, a reservoir characteristic may include the measured quantity of methane gas that was injected into the pore space. This measured gas, may provide an estimate of total gas in place for a particular reservoir from which the rock core was cored from. The uncorrupted NMR response may be analyzed and processed by any number of additional methods to further determine a reservoir characteristic. One such method, is to create an NMR spectra to determine the chemical shift of a sample. The chemical shift of a sample may be indicative of several factors relating to a reservoir characteristic, including estimating a porosity and viscosity.

Other methods to determine a reservoir characteristic may include analyzing the T1 signal values and T2 signal amplitudes from the NMR analysis to determine porosity or permeability. Determining the porosity of a rock core sample may indicate the capacity of a reservoir, from which the rock core sample was extracted from, to contain or store fluids including hydrocarbons. Determining the permeability of a rock core sample will communicate the reservoirs' ability to transmit the fluids contained within the reservoir. These reservoir characteristics are pertinent in creating a reservoir model with a reservoir modeler.

In Step 420 a reservoir model is generated using a reservoir modeler based on the reservoir characteristic, in accordance with one or more embodiments. Turning back to FIG. 1, a reservoir modeler may comprise functionality creating a reservoir model to predict the flow of fluids, including hydrocarbon fluids such as oil and gas, through a formation composed of porous, permeable reservoir rocks. The reservoir modeler may combine information determined from well logs, geological models and any reservoir characteristics determined from NMR analyses on rock core samples as described in this method. The reservoir model may include information total hydrocarbon in place, where the hydrocarbons are located, and how effectively the hydrocarbons can potentially flow.

In Step 422 a reservoir simulation is performed, using a reservoir simulator, to determine a drilling target based on the reservoir model. The reservoir model, including information about the total hydrocarbon in place and the ability for that hydrocarbon to flow, may be used as an input to perform a reservoir simulation. A reservoir simulator, described in FIG. 1, may be used to perform a reservoir simulation to predict the behavior of rocks and fluid under various hydrocarbon recovery scenarios, allowing reservoir engineers to understand which recovery options offer the most advantageous hydrocarbon recovery plan for a given reservoir. A drilling target, or a chosen location to penetrate the hydrocarbon reservoir, may be determined through reservoir simulation by estimating the fluid flow within the reservoir given various drilling target scenarios. Drilling decisions including determining an updated drilling target, may be determined based at least part, on the reservoir simulation. In some embodiments, the reservoir modeler and/or the reservoir simulator may include a computer system that is similar to the computer system (702) described below with regard to FIG. 7 and the accompanying description.

In Step 424 a wellbore path may be planned using a wellbore path planning system to intersect the drilling target and a wellbore guided by the wellbore path may be drilled using a drilling system, in accordance with one or more embodiments. Prior to the commencement of drilling, a wellbore plan may be generated. The wellbore plan may include a starting surface location of the wellbore, or a subsurface location within an existing wellbore, from which the wellbore may be drilled. Further, the wellbore plan may include a terminal location that may intersect with the targeted hydrocarbon bearing formation and a planned wellbore path from the starting location to the terminal location. A wellbore planning system may be used to generate the wellbore plan. The wellbore planning system may comprise one or more computer processors in communication with computer memory containing the reservoir model, information relating to drilling hazards, and the constraints imposed by the limitations of the drillstring and the drilling system.

The wellbore planning system may further include dedicated software to determine the planned wellbore path and associated drilling parameters, such as the planned wellbore diameter, the location of planned changes of the wellbore diameter, the planned depths at which casing will be inserted to support the wellbore and to prevent formation fluids entering the wellbore, and the drilling mud weights (densities) and types that may be used during drilling the wellbore. A wellbore guided by the wellbore path may be drilled by a drilling system in accordance with one or more embodiments. A drilling system is illustrated and given in more detail in FIG. 6.

FIGS. 5A and 5B shows two NMR spectra measured on similar rock plug samples taken from the same rock. Both FIG. 5A and FIG. 5B display chemical shift determined from the NMR test on the horizontal axis (504) and intensity of NMR response on the vertical axis (502). Both spectra were obtained using a Bruker 500-megahertz (MHz) NMR spectrometer and a Daedalus Innovations LLC pressure cell. The pressure cell was composed of zirconia and had an outside diameter of 5 mm and an inside diameter of 3.6 mm. A rock plug sample had a diameter of 3.34 mm and a length of 4 centimeters (cm). The rock plug sample was cored from a shale formation known to be a hydrocarbon source rock.

FIG. 5A shows the NMR spectrum obtained using a traditional method, while FIG. 5B shows the NMR spectrum obtained using an embodiment of the invention described herein. In FIG. 5A, the NMR spectrum (506) was recorded using a traditional method. In this case, the sample was immersed within the pressure cell in methane. Methane saturated the sample (210) and filled the interior volume (212) of the pressure cell (202) not occupied by the sample (210). The NMR spectrum (506) was recorded with methane at a pressure of 75 PSI. The NMR spectrum (506) is displayed with chemical shift on the horizontal axis (504) and intensity of NMR response on the vertical axis (502). This NMR spectrum (506) is characterized by a broad region (507) of elevated intensity and a sharp peak (508) superimposed upon the broad region (507). NMR spectrum (506) corresponds to a methane filled pressure cell (202). Methane is a common hydrocarbon gas commonly used in studies of this nature. However, similar results may also be obtained using other hydrocarbon gases, such as ethane, and propane.

NMR spectrum (510), displayed in FIG. 5B, was measured with an embodiment of the method outlined in FIG. 4. NMR spectrum (510) was recorded using a similar rock sample plug drawn from the same rock used to obtain NMR spectrum (506). NMR spectrum (510) is characterized by a broad region of elevated intensity (514) similar to the broad region of elevated intensity (507) displayed in NMR spectrum (506). However, unlike NMR spectrum (506) there is no sharp peak present in NMR spectrum (510). A person of ordinary skill in the art will readily appreciate that the broad regions of elevated intensity (507, 514) are signals produce by methane within the pores of the sample, while the sharp peak (508) present in NMR spectrum (506) is produced by the large volume of methane present in the annulus (212) of the pressure cell (202) when a traditional method of recording the NMR spectrum is used. This sharp peak (508) constitutes noise added to the desired NMR spectrum signal and thus the uncorrupted NMR spectrum (510) obtained using the inventive method described in FIG. 4 represents a clear improvement over the traditional method.

An improved estimate of the reservoir characteristic may be obtained from the uncorrupted NMR spectrum (510). The reservoir characteristic may be more accurately estimated from the uncorrupted NMR spectrum (510) than from the traditional NMR spectrum (506). Similarly, when the reservoir characteristic is used as a component of a reservoir model forming an input to a reservoir simulator, the improved estimate of the reservoir characteristic may produce a more accurate reservoir simulation of future fluid flow within, and production from, the hydrocarbon reservoir. Decisions, including determining a drilling target, may be determined based on the reservoir simulation.

Figure 6:
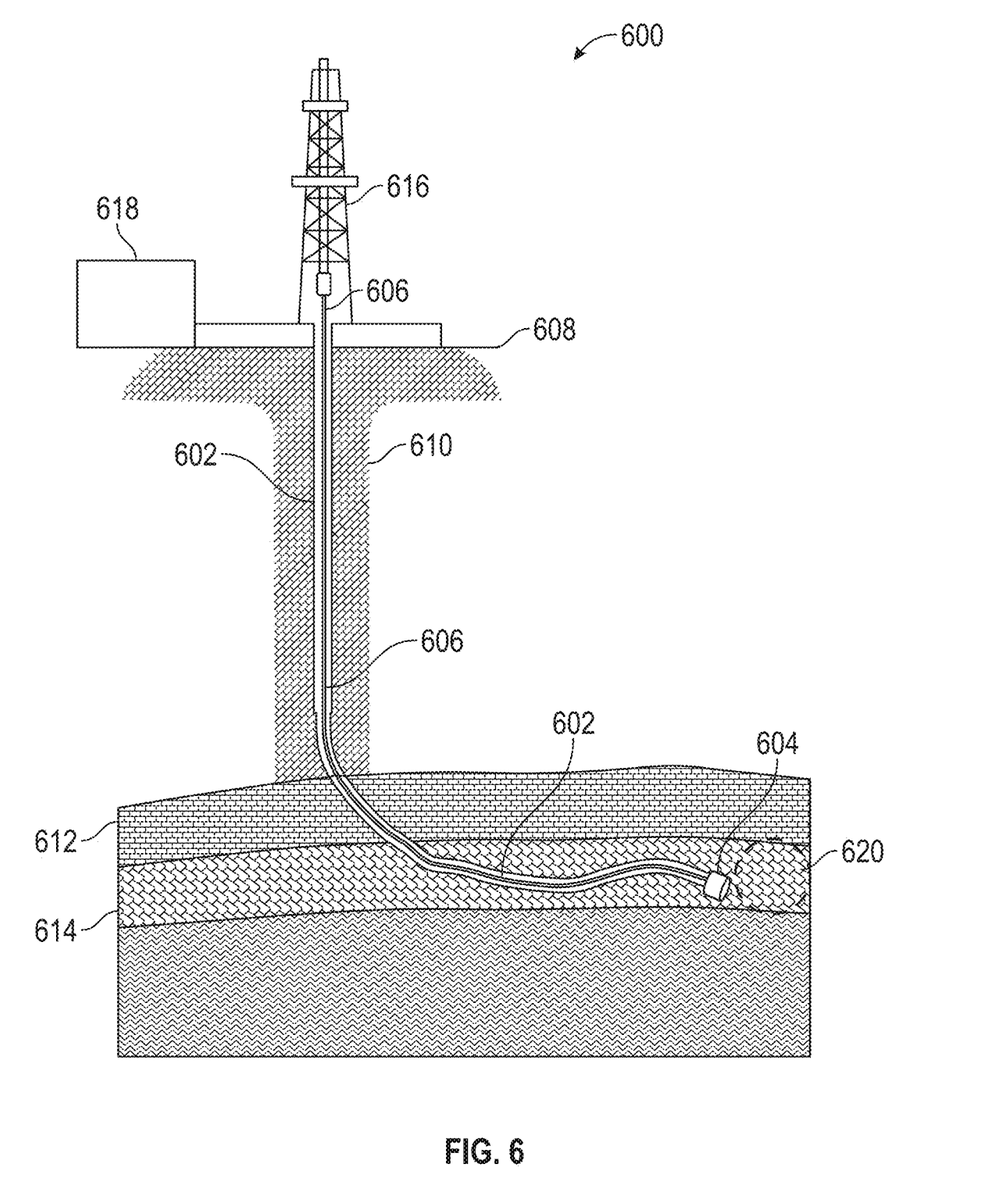
FIG. 6 depicts a drilling system in accordance with one or more embodiments.

FIG. 6 depicts a drilling system (600) in accordance with one or more embodiments. As shown in FIG. 6 a well path (602) may be drilled by a drill bit (604) attached by a drillstring (606) to a drill rig (616) located on the surface of the Earth (608). The well may traverse a plurality of overburden layers (610) and one or more cap-rock layers (612) to a drilling target (620) within a hydrocarbon reservoir (614). The well path (602) may be a curved well path, or a straight well path. All or part of the well path (602) may be vertical, and some well paths may be deviated or have horizontal sections.

Prior to the commencement of drilling, a wellbore plan may be generated. The wellbore plan may include a starting surface location of the wellbore, or a subsurface location within an existing wellbore, from which the wellbore may be drilled. Further, the wellbore plan may include a drilling target (620) and a planned wellbore path from the starting location to the drilling target.

Typically, the wellbore plan is generated based on best available information from a geophysical model associated with the geo-physical properties of the subsurface (e.g., wave speed or velocity, density, attenuation, anisotropy), geomechanical models encapsulating subterranean stress conditions, the trajectory of any existing wellbores (which it may be desirable to avoid), and the existence of other drilling hazards, such as shallow gas pockets, over-pressure zones, and active fault planes. Furthermore, the wellbore plan may take into account other engineering constraints such as the maximum wellbore curvature ("dog-log") that the drillstring may tolerate and the maximum torque and drag values that the drilling system may tolerate.

A wellbore planning system (618) may be used to generate the wellbore plan based on the drilling target (620) determined by the reservoir simulation. The reservoir simulation has predicted the flow of fluids through the reservoir formation, and an advantageous wellbore path to the drilling target (620) may be planned to extract the hydrocarbons. The wellbore planning system (618) may comprise one or more computer processors in communication with computer memory containing the geophysical and geomechanical models, the reservoir simulation, information relating to drilling hazards, and the constraints imposed by the limitations of the drillstring (606) and the drilling system (600). The wellbore planning system (618) may further include dedicated software to determine the planned wellbore path and associated drilling parameters, such as the planned wellbore diameter, the location of planned changes of the wellbore diameter, the planned depths at which casing will be inserted to support the wellbore and to prevent formation fluids entering the wellbore, and the drilling mud weights (densities) and types that may be used during drilling the wellbore.

Figure 7:
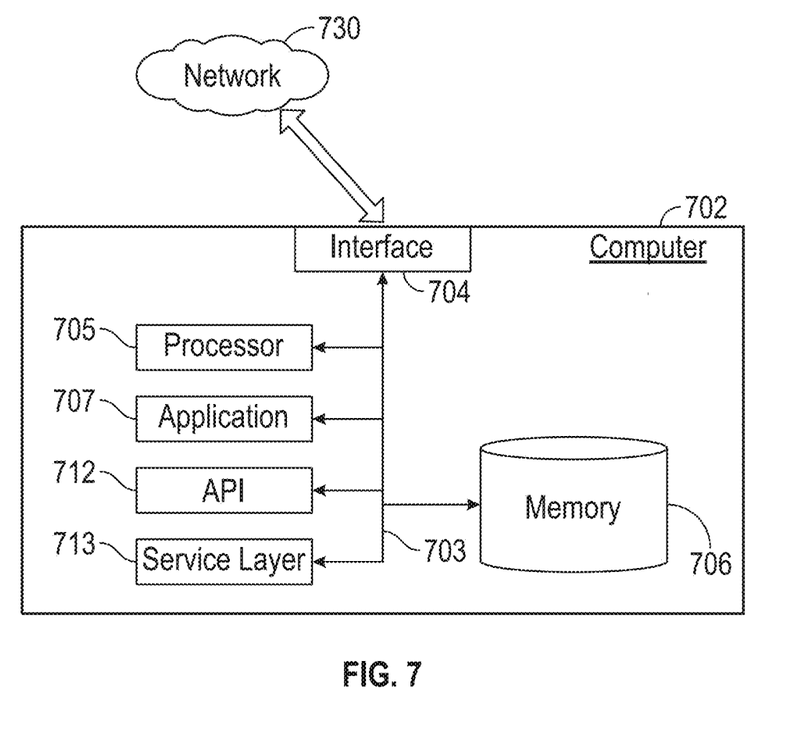
FIG. 7 depicts a computer system in accordance with one or more embodiments.

FIG. 7 depicts a block diagram of a computer system used to provide computational functionalities associated with described algorithms, methods, functions, processes, flows, and procedures as described in this disclosure, according to one or more embodiments. The illustrated computer (702) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or another suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (804) includes logic encoded in software or hardware (or a combination of software and hardware) and operable to communicate with the network (730). More specifically, the interface (804) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), wherein each computer (702) communicates over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

In some embodiments, an NMR system may perform NMR experiments using a first computer (702) and one or more first Applications (707) while the reservoir simulation may be conducted on a second computer (702) using one or more second Applications (707).

Although only a few example embodiments have been described in detail above, those skilled in the art will readily appreciate that many modifications are possible, including dimensions, in the example embodiments without materially departing from this invention. Accordingly, all such modifications are intended to be included within the scope of this disclosure as defined in the following claims.

What is claimed is:

1. A method for determining an uncorrupted nuclear magnetic resonance (NMR) response from a sample at a predetermined measurement pressure, comprising:
obtaining the sample;
obtaining a filler fluid, wherein the filler fluid has a negligible NMR response;
determining a volume of filler fluid based on a dimension of the sample and an interior volume of a pressure cell;
introducing the volume of filler fluid into the pressure cell, wherein the volume of filler fluid is at a first temperature;
changing the temperature of the volume of filler fluid to a second temperature;
inserting the sample into the volume of filler fluid within the pressure cell, displacing an upper surface of filler fluid to a predetermined level within the interior volume of the pressure cell, wherein the predetermined level is located above a top NMR coil surface and below a top surface of the sample;
establishing the predetermined measurement pressure within the pressure cell; and
determining the uncorrupted NMR response from the sample at the predetermined measurement pressure.

2. The method of claim 1, further comprising determining a reservoir characteristic of the sample based, at least in part, on the uncorrupted NMR response, wherein the reservoir characteristic comprises a porosity, a composition, a water and a hydrocarbon content, a permeability, or a behavior of an injected fluid.

3. The method of claim 2, further comprising:
generating a reservoir model using a reservoir modeler based, at least in part, on the reservoir characteristic;
performing a reservoir simulation, using a reservoir simulator, to determine a drilling target based, at least in part, on the reservoir model;
planning a wellbore path using a wellbore path planning system to intersect the drilling target; and
drilling a wellbore guided by the wellbore path using a drilling system.

4. The method of claim 2, wherein the injected fluid is not dissolvable in a filler fluid at the predetermined measurement pressure.

5. The method of claim 1, wherein the sample is a rock core sample.

6. The method of claim 1, wherein the filler fluid comprises a hydrogen-free filler fluid.

7. The method of claim 6, wherein the hydrogen-free filler fluid comprises Halocarbon 1000N.

8. The method of claim 1, wherein the predetermined measurement pressure comprises a hydrocarbon reservoir pressure.

9. The method of claim 1, wherein inserting the sample into the pressure cell further comprises inserting the sample through an open end of the pressure cell into the filler fluid disposed at a closed end of the pressure cell.

10. The method of claim 1, wherein a viscosity of the filler fluid at the first temperature is sufficiently low to enable an injection of the filler fluid into the pressure cell and the viscosity of the filler fluid at the second temperature is sufficiently high to prevent invasion of the filler fluid into pores within the sample.

11. An NMR system, comprising:
a pressure cell comprising a sealable open end, a closed end, and an interior volume;
a volume of filler fluid configured to be introduced injected inside the interior volume of the pressure cell at a first temperature, wherein a filler fluid has a negligible NMR response;
a sample, configured to be insertable into the pressure cell through the sealable open end and into the filler fluid at a second temperature, wherein the sample displaces an upper surface of filler fluid to a predetermined level within the interior volume of the pressure cell, wherein the predetermined level is located above a top NMR coil surface and below a top surface of the sample;
an NMR pressure and injection system configured to establish a predetermined measurement pressure within the pressure cell; and
an NMR control and data acquisition system configured to:
determine an uncorrupted NMR response from the sample at the predetermined measurement pressure, and
determine a reservoir characteristic of the sample based, at least in part, on the uncorrupted NMR response, wherein the reservoir characteristic comprises a porosity, a composition, a water and a hydrocarbon content, a permeability, or a behavior of an injected fluid.

12. The system of claim 11, further comprising:
a reservoir modeler configured to produce a reservoir model based, at least in part, on the reservoir characteristic;
a reservoir simulator configured to:
produce a reservoir simulation based, at least in part, on the reservoir model, and
determine a drilling target based, at least in part, on the reservoir simulation;
a wellbore path planning system configured to plan a wellbore path to intersect the drilling target of a subterranean region of interest; and
a wellbore drilling system configured to drill a wellbore guided by the wellbore path.

13. The system of claim 11, wherein the injected fluid is not dissolvable in the filler fluid at the measurement pressure.

14. The system of claim 11, wherein the volume of filler fluid is determined based on a dimension of the sample and the interior volume of the pressure cell.

15. The system of claim 11, wherein the sample is a rock core sample and the predetermined measurement pressure comprises a hydrocarbon reservoir pressure.

16. The system of claim 11, wherein the filler fluid comprises a hydrogen-free filler fluid.

17. The system of claim 16, wherein the hydrogen-free filler fluid comprises Halocarbon 1000N.

18. The system of claim 11, wherein a viscosity of the filler fluid at the first temperature is sufficiently low to enable injection of the filler fluid into the pressure cell and the viscosity of the filler fluid at the second temperature is sufficiently high to prevent invasion of the filler fluid into pores within the sample.

* * * * *